(12) United States Patent
Mouser (10) Patent No.: US 10,849,952 B2
(45) Date of Patent: *Dec. 1, 2020

(54) HAND SANITIZER COMPOSITION AND METHOD OF MANUFACTURE

(71) Applicant: Roger Wilson, Boise, ID (US)

(72) Inventor: Glen Mouser, Boise, ID (US)

(73) Assignee: Roger Wilson, Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/673,834

(22) Filed: Nov. 4, 2019

(65) Prior Publication Data
US 2020/0069761 A1 Mar. 5, 2020

Related U.S. Application Data

(63) Continuation of application No. 15/675,560, filed on Aug. 11, 2017, now Pat. No. 10,561,698, which is a
(Continued)

(51) Int. Cl.
| | | |
|---|---|---|
| *A61K 36/886* | (2006.01) |
| *A01N 33/12* | (2006.01) |
| *A61K 8/34* | (2006.01) |
| *A61K 8/365* | (2006.01) |
| *A61K 8/41* | (2006.01) |
| *A61K 31/728* | (2006.01) |

(Continued)

(52) U.S. Cl.
CPC ............ *A61K 36/886* (2013.01); *A01N 33/12* (2013.01); *A61K 8/342* (2013.01); *A61K 8/365* (2013.01); *A61K 8/41* (2013.01); *A61K 8/416* (2013.01); *A61K 9/06* (2013.01); *A61K 9/122* (2013.01); *A61K 31/198* (2013.01); *A61K 31/355* (2013.01); *A61K 31/4166* (2013.01); *A61K 31/728* (2013.01); *A61K 47/02* (2013.01); *A61K 47/10* (2013.01); *A61K 47/186* (2013.01); *A61K 47/26* (2013.01); *A61K 47/32* (2013.01); *A61K 47/34* (2013.01); *A61K 47/38* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 6,087,400 A | 7/2000 | Dyer et al. |
| 6,846,846 B2 | 1/2005 | Modak et al. |

(Continued)

*Primary Examiner* — Kyung S Chang
(74) *Attorney, Agent, or Firm* — Jason P. Webb; Pearson Butler (57) ABSTRACT

A hand sanitizing composition and a method of manufacture, wherein the composition includes a solvent from about 78% to about 96% by weight sufficient to operate as a carrier and solvent. The composition includes tetrasodium EDTA and/or Sodium Citrate from about 0.01% to about 1% by weight to operate as a buffer, stabilizer and chelating agent. The composition includes a humectant selected from the group of humectants consisting of: Cetyl Alcohol, Ceteryl Alcohol, and Steryl Alcohol from about 1.5% to about 5.5% by weight to emulsify, thicken and lubricate. The composition includes an emollient from about 0.1% to about 3.2% by weight and an antioxidant vitamin from about 0.01% to about 1% by weight. The composition includes a soothing agent in a therapeutically significant amount and a conditioner.

18 Claims, 2 Drawing Sheets

Related U.S. Application Data continuation-in-part of application No. 15/088,553, filed on Apr. 1, 2016, now Pat. No. 9,775,346.

(60) Provisional application No. 62/141,533, filed on Apr. 1, 2015.

(51) Int. Cl.

| | | |
|---|---|---|
| *A61K 31/335* | (2006.01) | |
| *A61K 47/38* | (2006.01) | |
| *A61K 31/198* | (2006.01) | |
| *A61Q 19/10* | (2006.01) | |
| *A61Q 17/00* | (2006.01) | |
| *A61K 31/4166* | (2006.01) | |
| *A61K 31/355* | (2006.01) | |
| *A61K 47/18* | (2017.01) | |
| *A61K 47/10* | (2017.01) | |
| *A61K 47/26* | (2006.01) | |
| *A61K 47/02* | (2006.01) | |
| *A61K 47/34* | (2017.01) | |
| *A61K 47/32* | (2006.01) | |
| *A61K 9/12* | (2006.01) | |
| *A61K 9/06* | (2006.01) | |

(56) References Cited

U.S. PATENT DOCUMENTS

| | | |
|---|---|---|
| 8,802,607 B2 | 8/2014 | Fan et al. |
| 8,865,195 B2 | 10/2014 | Wolff et al. |
| 2007/0241306 A1 | 10/2007 | Wehner et al. |
| 2008/0213192 A1 | 9/2008 | Schlesinger et al. |
| 2009/0175808 A1 | 7/2009 | Galley et al. |
| 2009/0226498 A1 | 9/2009 | Flugge-Berendes et al. |
| 2010/0316747 A1 | 12/2010 | Ge et al. |
| 2011/0207832 A1 | 8/2011 | Roszell et al. |
| 2011/0262558 A1 | 10/2011 | Huckfeldt et al. |
| 2012/0034314 A1 | 2/2012 | Levison et al. |
| 2013/0287712 A1 | 10/2013 | Wolff et al. |
| 2014/0017184 A1 | 1/2014 | Fumagalli et al. |
| 2014/0171513 A1 | 6/2014 | Seidling et al. |
| 2014/0315995 A1 | 10/2014 | Dreher |
| 2014/0364509 A1 | 12/2014 | Wegner et al. |
| 2015/0272124 A1 | 10/2015 | Pedersen et al. |

HAND SANITIZER COMPOSITION AND METHOD OF MANUFACTURE

CROSS-REFERENCE TO RELATED APPLICATIONS

This application is a Continuation Application of, under 35 U.S.C. § 121, and claims priority to, under 35 U.S.C. § 121, U.S. Continuation in Part application Ser. No. 15/675,560, entitled HAND SANITIZER COMPOSITION AND METHOD OF MANUFACTURE, by Glen Mouser filed on Aug. 11, 2017 This invention claims priority, under 35 U.S.C. § 120, to the U.S. Non-Provisional patent application Ser. No. 15/088,553 by Glen Mouser filed on Apr. 1, 2016, which is incorporated by reference herein and therethrough under 35 U.S.C. § 120, to U.S. Provisional Patent Application No. 62/141,533 to Glen Mouser filed on Apr. 1, 2015, which is incorporated by reference herein in its entirety.

BACKGROUND OF THE INVENTION

Field of the Invention

The present invention relates to sanitizers, specifically a hand sanitizer composition and method of manufacture.

Description of the Related Art

A hand antiseptic, hand disinfectant, or hand sanitizer is a supplement or alternative to hand washing with soap and water. Many preparations are available, including gel, form, and liquid solutions. The active ingredient in hand sanitizers may be isopropyl alcohol (isopropanol), ethanol, n-propanol, or povidone-iodine. Inactive ingredients in alcohol rubs typically include a thickening agent such as polyacrylic acid for alcohol gels, humectants such as glycerin for liquid rubs, propylene glycol, and essential oils of plants. Alcohol-based hand sanitizers are more effective at killing microorganisms than soaps and do not dry out hands as much.

Common non-alcohol, rinse-free hand sanitizers use either small concentrations of the nitrogenous cationic surface-acting agent benzalkonium chloride, the chlorinated aromatic compound triclosan, or povidone-iodine. Some products claim to kill microorganisms naturally, although these claims are not substantiated in any FDA monograph. All hand sanitizer products require National Drug Code designation in the United States and natural product number designation in Canada.

Some improvements have been made in the field. Examples of references related to the present invention are described below in their own words, and the supporting teachings of each reference are incorporated by reference herein:

U.S. Pat. No. 8,865,195, issued to Wolff et al., discloses forming formulations including silicone polyesters are disclosed. These forming formulations are useful as cleansing formulations such as used in liquid hand cleansers and wet wipes. The forming formulations provide improved aesthetic properties and forming appearance, while maintaining high antimicrobial capacity.

U.S. Pat. No. 6,846,846, issued to Modak et al., discloses antimicrobial compositions having synergistic combinations of octoxyglycerin and at least one other antimicrobial agent in formulations which are more effective than prior art compositions without causing increased irritation to the skin of the average user. In certain embodiments, skin irritation may be minimized by low concentrations of antimicrobials and/or the presence of soothing compounds such as zinc. Preferred embodiments include combinations of octoxyglycerin, a quaternary compound, and at least one other antimicrobial agent. Without being bound to any particular theory, it is hypothesized that the unexpected antimicrobial effectiveness of combinations of octoxyglycerin may result from an enhancement of the permeability of microbes to antimicrobials caused by octoxyglycerin.

U.S. Pat. No. 6,087,400, issued to Dyer et al., discloses antimicrobial compositions and methods for preparing and using same are provided. The antimicrobial compositions are surfactant-based and contain certain benzalkonium chloride homologs. The compositions are useful in treating infections in animals and humans, and can be applied to areas including the skin, nails, and mouth.

U.S. Patent Application Publication No.: 2015/0272124, by Pedersen et al., discloses an antimicrobial composition of the present invention comprises a cationic active ingredient, a form boosting surfactant, a form boosting copolymer, a form stabilizer, and a chelating agent. The present antimicrobial compositions are free of the antimicrobial agent triclosan (i.e., 2,4,4'-trichloro-2'hydroxy-diphenylether), have rapid cidal activity, provide stable copious form and exhibit enhanced tissue (e.g. skin) compatibility as defined by an in vitro whole toxicology assessment method.

U.S. Patent Application Publication No.: 2011/0262558, by Huckfeldt et al., discloses an improved composition for skin cleansing and protection is disclosed. The composition contains an effective amount of at least one alpha-hydroxyl acid or a pharmaceutically acceptable salt thereof, at least one base, one surfactant and one skin protectant. Various additives and excipients may be included in the formulation. The improved composition disclosed herein achieves a higher bacteria killing rate and shows longer action duration. The disclosed composition is capable of penetrating deep into the skin which allows for delivery of more antimicrobials to sites that are at a higher risk of being infected. Various modifications of the improved composition are also disclosed.

U.S. Patent Application Publication No.: 2009/0226498, by Flugge-Berendes et al., discloses moisturizing hand sanitizers including alcohols that are effective in killing microorganisms while providing a moisturizing benefit to the user's skin. More particularly, the alcohol-based hand sanitizers include a high internal phase emulsion which allows moisturizers or skin protectants such as emollients and/or silicones to be stably incorporated into the sanitizer.

The inventions heretofore known suffer from a number of disadvantages which include being limited in composition, being limited in use, being limited in ingredients, being limited in effectiveness, being limited in efficiency, being expensive, being limited in application, and the like.

What is needed is a hand sanitizer, sanitizing composition, and/or method of manufacture of the same that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available hand sanitizers. Accordingly, the present invention has been developed to provide an effective and efficient hand sanitizer.

According to one embodiment of the invention, there is a hand sanitizing composition that may include a solvent from about 78% to about 96% by weight sufficient to operate as a carrier and solvent for the composition. The composition may include tetrasodium EDTA and/or Sodium Citrate from about 0.01% to about 1% by weight to operate as a buffer, stabilizer and chelating agent. The composition may include a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition may include an emollient from about 0.1% to about 3.2% by weight. The composition may include an antioxidant vitamin from about 0.01% to about 1% by weight. The composition may include a soothing agent in a therapeutically significant amount. The hand sanitizing composition may include a conditioner selected from the group of conditioners consisting of: Stearylkonium Chloride, Behentrimonium Chloride and Cetrimonium Chloride from an amount of about 0.1% to about 3.1% by weight.

The hand sanitizing composition may include a non-ionic surfactant from about 0.02% to about 7.9% by weight. The composition may include a preservative from about 0.1% to about 1.8% by weight. The composition may include a sanitizer selected from the group of sanitizers consisting of: Benzalkonium Chloride and Benzathonium Chloride from an amount of about 0.01% to about 0.13% by weight sufficient to sanitize hands during the use of the composition. The composition may include a biostatic antimicrobial.

According to one embodiment of the invention, there is a hand sanitizing composition that may consist essential of a solvent from about 78% to about 96% by weight sufficient to operate as a carrier and solvent for the composition. The composition may include tetrasodium EDTA and/or Sodium Citrate from about 0.01% to about 1% by weight to operate as a buffer, stabilizer and chelating agent. The composition may include a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition may include an emollient from about 0.1% to about 3.2% by weight. The composition may include an antioxidant vitamin from about 0.01% to about 1% by weight. The composition may include a soothing agent in a therapeutically significant amount. The composition may include a conditioner selected from the group of conditioners consisting of: Stearylkonium Chloride, Behentrimonium Chloride and Cetrimonium Chloride from an amount of about 0.1% to about 3.1% by weight.

The hand sanitizing composition may include a non-ionic surfactant from about 0.02% to about 7.9% by weight. The composition may include a preservative from about 0.1% to about 1.8% by weight. The composition may include a sanitizer selected from the group of sanitizers consisting of: Benzalkonium Chloride and Benzathonium Chloride from an amount of about 0.01% to about 0.13% by weight sufficient to sanitize hands during the use of the composition.

According to one embodiment of the invention, there is a method of manufacturing a hand sanitizer that may include the steps of mixing together in a vessel, using heat as needed a solvent from about 78% to about 96% by weight sufficient to operate as a carrier and solvent for the composition; and tetrasodium EDTA and/or Sodium Citrate from about 0.01% to about 1% by weight to operate as a buffer, stabilizer and chelating agent.

The method of manufacturing a hand sanitizer may include the step of adding the following ingredients and homogenizing a humectant selected from the group of humectants consisting of: Cetyl Alcohol, Ceteryl Alcohol, and Steryl Alcohol from about 1.5% to about 5.5% by weight to emulsify, thicken and lubricate; an emollient from about 0.1% to about 3.2% by weight; an antioxidant vitamin from about 0.01% to about 1% by weight; a soothing agent in a therapeutically significant amount; a conditioner selected from the group of conditioners consisting of: Stearylkonium Chloride, Behentrimonium Chloride and Cetrimonium Chloride from an amount of about 0.1% to about 3.1% by weight; a non-ionic surfactant from about 0.02% to about 7.9% by weight; and a preservative from about 0.1% to about 1.8% by weight.

The method of manufacturing a hand sanitizer may include the step of adding, sufficiently slowly while mixing to prevent undesired effects, a sanitizer selected from the group of sanitizers consisting of: Benzalkonium Chloride and Benzathonium Chloride from an amount of about 0.01% to about 0.13% by weight sufficient to sanitize hands during the use of the composition.

According to yet another embodiment of the invention, there is a hand sanitizing composition. The composition may be embodied as a forming composition, a gel composition, and/or a lotion composition. The composition may include one or more of: water as a solvent and carrier from about 60% to about 96% by weight sufficient to operate as a carrier and solvent for the composition; Tetrasodium EDTA from about 0.001% to about 0.1%, by weight; Benzathonium Chloride as a preservative from about 0.1% to about 1.0% by weight; a conditioner selected from the group of conditioners consisting of: Stearylkonium Chloride, Behentrimonium Chloride and Cetrimonium Chloride from an amount of about 0.1% to about 9% by weight; Glycerin from about 0.1% to about 1.4% by weight; a surfactant from about 0.02% to about 7.9% by weight; mineral salts from about 0.1% to about 1.4% by weight; a skin protectant from about 0.1% to about 1.4% by weight; an antioxidant vitamin from about 0.01% to about 1.4% by weight; Aloe Vera gel from about 0.1% to about 1.4% by weight; Hyaluronic Acid from about 0.02% to about 2.0% by weight; Cocamidopropyl Betaine from about 0.4% to about 3.0% by weight; Behentrimonium Methosulfate from about 1.0% to about 9.0% by weight; Dimethicone from about 0.5% to about 4.0% by weight; Hydroxyethyl Ethylcellusose from about 0.1% to about 2.4% by weight; Phenoxyehtanol from about 0.1% to about 1.4% by weight; Caprylyl Glycol from about 0.1% to about 1.4% by weight; Carbomer from about 0.01% to about 1.4% by weight; and/or Benzalkonium Chloride from about 0.01% to about 0.13% by weight, sufficient to sanitize hands during the use of the composition.

It may be that the conditioner is Cetrimonium Chloride in an amount of between about 1% and about 9% by weight. It may be that the surfactant is Polysorbate 20 in an amount of between about 0.1% to about 1.4% by weight. It may be that the mineral salts includes one or more of: Calcium Fluoride, Calcium Phosphate, Calcium Sulphate, Iron Phosphate, Potassium Chloride, Potassium Phosphate, Potassium Sulphate, Magnesium Phosphate, Sodium Chloride, Sodium Phosphate, Sodium Sulphate, and Silicon Dioxide. It may be that the skin protectant is Allantoin. It may be that the antioxidant vitamin is Vitamin E Acetate.

In still yet another further non-limiting embodiment, there is a forming, lotion, and/or gel hand sanitizing composition, consisting essentially of one or more of: water as a solvent and carrier from about 60% to about 96% by weight sufficient to operate as a carrier and solvent for the composition; Tetrasodium EDTA from about 0.001% to about 0.1%, by weight; Benzathonium Chloride as a preservative from about 0.1% to about 1.0% by weight; a conditioner selected from the group of conditioners consisting of: Stearylkonium Chloride, Behentrimonium Chloride and Cetrimonium Chloride from an amount of about 0.1% to about 9% by weight; Glycerin from about 0.1% to about 1.4% by weight; a surfactant from about 0.02% to about 7.9% by weight; mineral salts from about 0.1% to about 1.4% by weight; a skin protectant from about 0.1% to about 1.4% by weight; an antioxidant vitamin from about 0.01% to about 1.4% by weight; and/or Benzalkonium Chloride from about 0.01% to about 0.13% by weight, sufficient to sanitize hands during the use of the composition.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

The term "about," as used herein, modifying the quantity of an ingredient in the compositions of the invention or employed in the methods of the invention refers to variation in the numerical quantity that can occur, for example, through typical measuring and liquid handling procedures used for making concentrates or use solutions; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Figure 1:
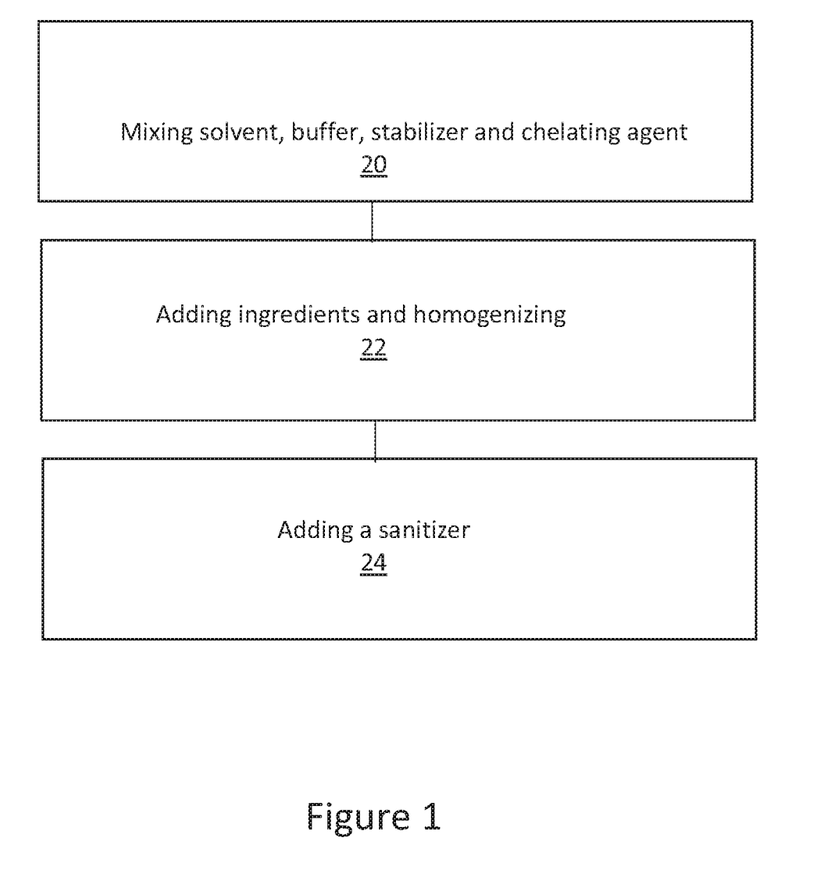
FIG. 1 is a flowchart of a method of manufacturing a hand sanitizer, according to one embodiment of the invention.

FIG. 1 is a flowchart of a method of manufacturing a hand sanitizer, according to one embodiment of the invention. There is shown a method of manufacturing a hand sanitizer including the following steps.

The illustrated method of manufacturing a hand sanitizer includes the step of mixing together in a vessel, using heat as needed, a solvent from about 78% to about 96% by weight sufficient to operate as a carrier and solvent for the composition and adding tetrasodium EDTA and/or Sodium Citrate from about 0.01% to about 1% by weight to operate as a buffer, stabilizer and chelating agent to the solvent 20.

The method of manufacturing a hand sanitizer includes the step of adding the following ingredients and homogenizing a humectant selected from the group of humectants consisting of: Cetyl Alcohol, Ceteryl Alcohol, and Steryl Alcohol from about 1.5% to about 5.5% by weight to emulsify, thicken and lubricate; an emollient from about 0.1% to about 3.2% by weight; an antioxidant vitamin from about 0.01% to about 1% by weight; a soothing agent in a therapeutically significant amount; a conditioner selected from the group of conditioners consisting of: Stearylkonium Chloride, Behentrimonium Chloride and Cetrimonium Chloride from an amount of about 0.1% to about 3.1% by weight; a non-ionic surfactant from about 0.02% to about 7.9% by weight; and a preservative from about 0.1% to about 1.8% by weight, and/or any other ingredients described in this application in amounts as described.

The method of manufacturing a hand sanitizer may include the step of adding, sufficiently slowly while mixing to prevent undesired effects, a sanitizer selected from the group of sanitizers consisting of: Benzalkonium Chloride and Benzathonium Chloride from an amount of about 0.01% to about 0.13% by weight sufficient to sanitize hands during the use of the composition.

According to one embodiment of the invention, there is a hand sanitizing composition that includes a solvent from about 78% to about 96% by weight sufficient to operate as a carrier and solvent for the composition. The composition includes tetrasodium EDTA and/or Sodium Citrate from about 0.01% to about 1% by weight to operate as a buffer, stabilizer and chelating agent. The composition includes a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition includes an emollient from about 0.1% to about 3.2% by weight. The composition includes an antioxidant vitamin from about 0.01% to about 1% by weight. The composition includes a soothing agent in a therapeutically significant amount. The hand sanitizing composition includes a conditioner selected from the group of conditioners consisting of: Stearylkonium Chloride, Behentrimonium Chloride and Cetrimonium Chloride from an amount of about 0.1% to about 3.1% by weight.

The hand sanitizing composition includes a non-ionic surfactant from about 0.02% to about 7.9% by weight. The composition includes a preservative from about 0.1% to about 1.8% by weight. The composition includes a sanitizer selected from the group of sanitizers consisting of: Benzalkonium Chloride and Benzathonium Chloride from an amount of about 0.01% to about 0.13% by weight sufficient to sanitize hands during the use of the composition. The composition includes a biostatic antimicrobial. The biostatic antimicrobial may be such as that produced under the brand name BioProtect (aka antimicrobial silicon quat) by Chemex Industries, Inc. of Irvine Calif.

According to one embodiment of the invention, there is a hand sanitizing composition that is consisting essential of a solvent from about 78% to about 96% by weight sufficient to operate as a carrier and solvent for the composition. The composition includes tetrasodium EDTA and/or Sodium Citrate from about 0.01% to about 1% by weight to operate as a buffer, stabilizer and chelating agent. The composition includes a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition includes an emollient from about 0.1% to about 3.2% by weight. The composition includes an antioxidant vitamin from about 0.01% to about 1% by weight. The composition includes a soothing agent in a therapeutically significant amount. The composition includes a conditioner selected from the group of conditioners consisting of: Stearylkonium Chloride, Behentrimonium Chloride and Cetrimonium Chloride from an amount of about 0.1% to about 3.1% by weight.

The hand sanitizing composition includes a non-ionic surfactant from about 0.02% to about 7.9% by weight. The composition includes a preservative from about 0.1% to about 1.8% by weight. The composition includes a sanitizer selected from the group of sanitizers consisting of: Benzalkonium Chloride and Benzathonium Chloride from an amount of about 0.01% to about 0.13% by weight sufficient to sanitize hands during the use of the composition.

According to one embodiment of the invention, there is a hand sanitizer lotion that may be of medical grade and/or may be for personal use and/or for use by medical personnel. A formula may, when combined as explained, offer a high degree of bactericidal efficacy. The formula may be a cold or hot mix formula based upon ingredients chosen as some ingredients will mix better when heat is applied before, during and/or after the mixing thereof.

The formula includes one or more of: Water from about 78 to about 96% by weight to operate as an excipient, carrier and/or a solvent; Tetrasodium EDTA (a chelating agent) and/or Sodium Citrate from about 0.01 to about 1% by weight to operate as a buffer, water stabilizer, pH stabilizer, chelating agent and/or to otherwise influence the mixing, emulsification, acidity regulation, and/or the like thereof of the mixture; Cetyl Alcohol and/or Ceteryl Alcohol and/or Steryl Alcohol from about 1.5% to about 5.5% by weight to emulsify, serve as a humectant, thicken, and/or lubricate; Dimethicone (silicone) and/or an ester similar Octyl Palmitate and/or Isopropyl Myristate and/or Sorbitan Laurate from about 0.1 to about 3.2% to serve as an emollient, glide, protectant and/or body builder; Vitamin E Tocopherol and/or Vitamin A Palmitate from about 0.01 to about 1% by weight to serve as an antioxidant, emollient and/or a humectant: Hyaluronic Acid or Glycerin and/or Aloe Vera and/or similar humectant from about 0.001 to about 1.2% by weight to serve as a soothing agent, humectant, and/or thickener; Stearylkonium Chloride and/or Behentrimonium Chloride and/or Cetrimonium chloride from about 0.1 to about 3.1% by weight to serve as a conditioner and/or a stabilizer; a surfactant that is cationic and/or non-ionic such but not limited to a polysorbate 20, 60, 80 and/or cocamidopropyl betaine from about 0.02 to about 7.9% by weight to serve as a cleaner, detergent, surfactant, and/or emulsifier, a Preservative System (phenoxyethanol, caprylyl glycol, sorbic acid) and/or preservative similar and/or compatable with one or more ingredients from about 0.1 to about 1.8% by weight as a broad spectrum preservative; and/or Benzalkonium Chloride and/or Benzathonium Chloride from about 0.01 to about 0.13% by weight to serve as an Active Ingredient for the purpose of sanitizing hands.

To mix, perform one or more of the following steps: in an adequate vessel, put water and EDTA and mix; heat as necessary to melt or dissolve ingredients chosen; add balance of ingredients and high speed mix or homogenize until smooth; add the Active Ingredient very, very slowly and continue mixing until smooth; and/or pour off and fill containers.

According to yet another embodiment of the invention, there is a hand sanitizing composition. The composition may be embodied as a forming composition, a gel composition, and/or a lotion composition. The composition may include one or more of: water as a solvent and carrier between two of about 60%, 65%, 70%, 75%, 80%, 85%, 90%, and 96% by weight sufficient to operate as a carrier and solvent for the composition; Tetrasodium EDTA between two of about 0.001%, 0.005%, 0.01%, 0.05%, 0.06%, 0.07%, 0.08%, 0.09%, and 0.1%, by weight; Benzathonium Chloride as a preservative between two of about 0.1%, 0.2%, 0.3%, 0.4%, 0.5%, 0.6%, 0.7%, 0.8%, 0.9%, and 1.0% by weight; a conditioner that may be selected from the group of conditioners consisting of: Stearylkonium Chloride, Behentrimonium Chloride and Cetrimonium Chloride from an amount of between two of about 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, and 9% by weight; Glycerin between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; a surfactant from about 0.02% to about 7.9% by weight; mineral salts between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; a skin protectant between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; an antioxidant (may be a vitamin) between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; Aloe Vera gel between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; Hyaluronic Acid from about 0.02% to about 2.0% by weight; Cocamidopropoyl Betaine between two of about 0.4%, 0.5%, 0.6%, 0.7%, 0.8%, 0.9%, 1.0%, 1.1%, 1.2%, 1.3%, 1.4%, 1.5%, 2.0%, 2.5%, and 3.0% by weight; Behentrimonium Methosulfate between two of about 1.0%, 2.0%, 3.0%, 4.0%, 5.0%, 6.0%, 7.0%, 8.0%, and 9% by weight; Dimethicone between two of about 0.5%, 1.0%, 1.5%, 2.0%, 2.5%, 3.0%, 3.5% and 4.0% by weight; Hydroxyethyl Ethylcellusose between two of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, and 2.4% by weight; Phenoxyehtanol between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; Caprylyl Glycol between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; Carbomer between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight; and/or Benzalkonium Chloride from about 0.01%, 0.02%, 0.03%, 0.04%, 0.05%, 0.06%, 0.07%, 0.08%, 0.09%, 0.10%, 0.11%, 0.12%, and 0.13% by weight, sufficient to sanitize hands during the use of the composition.

Conditioner

It may be that the conditioner is Cetrimonium Chloride in an amount of between two of about 1.0%, 2.0%, 3.0%, 4.0%, 5.0%, 6.0%, 7.0%, 8.0%, and 9% by weight. The composition may include alternative/additional skin conditioner such as vitamins, a humectant, an occlusive agent, or other moisturizer to provide skin moisturizing, skin softening, skin barrier maintenance, anti-irritation, or other skin health benefits. Some non-limiting examples of additional skin conditioners include alkyl benzoate, myristyl myristate, cetyl myristate, gelatin, carboxylic acid, lsactoc acid, glyceryl dioleate, methyl laurate, PPG-9 laurate, lauryl lacylate allantoin, octyl palmitate, lanolin, propylene glycol, butylene glycol, ethylene glycol, caprylyl glycol, monobutyl ether, glycerine, fatty acids, proline, natural oils such as almond, mineral, canola, sesame, soybean, pyrrolidine, wheat germ, hydrolyzed wheat protein, hydrolyzed oat protein, hydrolyzed collagen, corn, peanut and olive oil, isopropyl myristate, myristyl alcohol, aloe vera, algae extract, gluconic acid, hydrolyzed silk protein, 1,3-propane-diol, Vitamin E, nicatinamide, stearyl alcohol, isopropyl palmitate, sorbitol, amino acid complexes, panthenol, allantoin, Dihydroxypropyltrimonium Chloride, quaternized hydrolyzed protein such as collagen, oat, wheat, etc . . . . , inositol, fructose, sucrose, hydrolyzed plant proteins, seaweed extract, polyethylene glycol, ammonium lactate, sodium hyaluronate, and cyclic peptides.

Some non-limiting examples of humectants include hydroxyethyl urea, agarose, urea, sodium PCA, arginine PCA, fructose, glucose, glutamic acid, glycerine, honey, lactose, maltose, polyethylene glycol, sorbitol and mixtures thereof.

Some non-limiting examples of occlusive agents include petrolatum, shea butter, avocado oil, balm mint oil, cod liver oil, mineral oil, trimyristin, stearyl stearate, synthetic wax, or mixtures thereof. Some non-limiting examples of other moisturizers include ethyl hexylglycerin, cholesterol, cystine, hyaluronic acid, keratin, lecithin, egg yolk, glycine, PPG-12, polyquaternium polymers such as polyquaternium-11, behentrimonium chloride, dihydroxypropyl PEG-5 linoleammonium chloride, glycerol oleate, PEG-7 glyceryl cocoate, cocoglucoside, PEG-200 hydrogenated glyceryl palmate, panthenol, retinol, salicylic acid, vegetable oil, methyl gluceth-10, methyl gluceth-20, ethoxylated derivatives of skin conditioners such as glycereth-26 and ethoxylated shea butter, and mixtures thereof. Finally, some non-limiting examples of anti-irritants include bisabolol and panthenol.

Preservative

The composition may include a preservative. Such may be Benzathonium Chloride from about 0.1% to about 1.0% by weight. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds, alkyl parabens, and miscellaneous compounds. Some non-limiting examples of phenolic antimicrobial agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof. Some non-limiting examples of halogen compounds include trichlorohydroxy diphenyl ether (Triclosan), sodium trichloroisocyanurate, sodium dichloroisocyanurate, iodine-poly(vinylpyrrolidin-onen) complexes, and bromine compounds such as 2-bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate. Some non-limiting examples of alkyl parabens include methyl, ethyl, propyl and butyl parabens.

Surfactant

It may be that the surfactant is Polysorbate 20 in an amount of between two of about 0.1%, 0.2%, 0.3%, 0.4%, 0.5%, 0.6%, 0.7%, 0.8%, 0.9%, 1.0%, 1.1%, 1.2%, 1.3%, and 1.4% by weight. The composition may contain a surfactant or surfactant mixture. These can be selected from water soluble or water dispersible nonionic, semi-polar nonionic, anionic, cationic, amphoteric, or zwitterionic surface-active agents; or any combination thereof. The particular surfactant or surfactant mixture chosen for use in the process and products of this invention can depend on the conditions of final utility, including method of manufacture, physical product form, use pH, and the like.

A typical listing of the classes and species of surfactants useful herein appears in U.S. Pat. No. 3,664,961 issued May 23, 1972, to Norris. The disclosure of which is hereby incorporated by reference. Additional surfactants, if present may be in the amount of from 0.5 to about 10 wt. %, from about 1.0 to about 7 wt. % and from about 2 to about 5 wt. %.

Mineral Salts

Mineral salts are inorganic salts that need to be ingested or absorbed by living organisms for healthy growth and/or maintenance. They may include salts of the trace elements in animals and/or micronutrients in plants. It may be that the mineral salts includes all, one, or more of: Calcium Fluoride, Calcium Phosphate, Calcium Sulphate, Iron Phosphate, Potassium Chloride, Potassium Phosphate, Potassium Sulphate, Magnesium Phosphate, Sodium Chloride, Sodium Phosphate, Sodium Sulphate, and Silicon Dioxide.

Skin Protectant

It may be that the skin protectant is Allantoin. Skin protectants may be used with skin conditioners or alone. Non-limiting examples of skin protectants include petroleum, cocoa butter, calamine, and kaolin. Additional examples of skin conditioners and protectants can be found in "CTFA Cosmetic Ingredient Handbook," J. M. Nikitakis, ed., The Cosmetic, Toiletry and Fragrance Association, Inc., Washington, D.C. (1988) (hereafter CTFA Handbook), pages 79-85, incorporated herein by reference.

Anti-Oxidants

Antioxidants neutralize free radicals that can damage skin cells, and include ascorbic acid (vitamin C), tocopherols (vitamin E), alpha lipoic acid, grape seed extract, green tea extract, L-ergothioneine and resveratrol. Examples of analgesics/anti-inflammatory agents include non-steroidal anti-inflammatory agents (e.g., ibuprofen, acetaminophen, ketoprofen, indomethacin, aspirin, and the like) and corticosteroids. It may be that the antioxidant vitamin is Vitamin E Acetate and/or its derivatives. There may be Vitamin C and/or its derivatives. There may be coenzyme Q $10^{th}$.

The composition may optionally include an antioxidant for improved skin condition through the removal of free radicals, and improved product stability. Some non-limiting examples of antioxidants include retinol and retinol derivatives, ascorbic acid and ascorbic acid derivatives, BHA, BHT, betacarotene, cysteine, erythorbic acid, hydroquinone, tocopherol and tocopherol derivatives, and the like.

If an antioxidant is included, it is preferably present in the composition in an amount from about 0.001 to about 2 wt. %, from about 0.01 to about 1 wt. %, and from about 0.05 to about 0.5 wt. %.

Additional functional ingredients may be used to improve the effectiveness of the composition. Some non-limiting examples of such additional functional ingredients include skin feel improvers, skin conditioners, surfactants pH adjusting compound, preservatives, antioxidants, fragrances, dyes, and the like, as well as mixtures thereof. The composition may optionally include a dye. Examples of dyes include any water soluble or product soluble dye, any FD&C or D&C approved dye.

The composition may optionally include a thickener. Exemplary thickeners include (1) cellulosic thickeners and their derivatives, (2) natural gums, (3) starches, (4) stearates, and (5) fatty acid alcohols, (6) acrylic acid polymers and crosspolymers (example "carbomer", (7) Aristoflex AVC (need generic category name) Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, and the like. Some non-limiting examples of fatty acid alcohols include caprylic alcohol, cetearyl alcohol, lauryl alcohol, oleyl alcohol, palm kernel alcohol, and the like.

The amount of thickener in the composition depends on the desired viscosity of the composition. The composition preferably has a viscosity low enough to pump through a former such as an Airspray former and allow forming.

The compositions of to the invention may be produced wherein a part of the water is supplied to a suitable mixing vessel further provided with a stirrer or agitator, and while stirring, the remaining constituents are added to the mixing vessel, including any final amount of water needed to provide to 100% wt. of the inventive composition. A sanitizing agent may be added last, and slowly, for best results.

The compositions may be packaged in any suitable container particularly flasks or bottles, including squeeze-type or pump bottles, as well as bottles provided with a spray apparatus (e.g. trigger spray) which is used to dispense the composition by spraying. The selected packaging may have a pump head former. Examples of commercially available pump head formers include the F2 former from Rexam PLC (London, England, formerly Airspray), and the RF-17 Palm Former from Rieke Corporation (Auburn, Ind.). Accordingly the compositions are desirably provided as a ready to use product in a manually operated dispensing container.

Whereas the compositions of the present invention are intended to be used in the types of liquid forms described, nothing in this specification shall be understood as to limit the use of the composition according to the invention with a further amount of water to form a solution there from. Conversely, nothing in the specification shall be also understood to limit the forming of a "super-concentrated" composition based upon the composition described above Such a super-concentrated ingredient composition is essentially the same as the compositions described above except in that they include a lesser amount of water.

In still yet another further non-limiting embodiment, there is a forming, lotion, and/or gel hand sanitizing composition, consisting essentially of one or more of: water as a solvent and carrier from about 60% to about 96% by weight sufficient to operate as a carrier and solvent for the composition; Benzathonium Chloride as a preservative from about 0.1% to about 1.0% by weight; a conditioner selected from the group of conditioners consisting of: Stearylkonium Chloride, Behentrimonium Chloride and Cetrimonium Chloride from an amount of about 0.1% to about 9% by weight; Glycerin from about 0.1% to about 1.4% by weight; a surfactant from about 0.02% to about 7.9% by weight; mineral salts from about 0.1% to about 1.4% by weight; a skin protectant from about 0.1% to about 1.4% by weight; an antioxidant vitamin from about 0.01% to about 1.4% by weight; and/or Benzalkonium Chloride from about 0.01% to about 0.13% by weight, sufficient to sanitize hands during the use of the composition.

The following are non-limiting exemplary embodiments of sanitizing compositions:

Former Sanitizer
Benzalkonium Chloride 0.13%
Water (60% to 95%)
Tetrasodium EDTA (0.001% to about 0.1%)
Cetrimonium Chloride (1% to 9%)
Cocamidopropoyl Betaine (0.4% to 3%)
Glycerin (0.1% to 1.4%)
Polysorbate 20 (0.1% to 1.4%)
12 cell building mineral salts (0.1% to 1.4%)
Allantoin (0.1% to 1.4%)
Aloe Vera Gel (0.1% to 1.4%)
Vitamin E Acetate (0.1% to 1.4%)
Benzathonium Chloride (0.1% to 1.0%)
Hyaluronic Acid (0.02% to 2.0%)
Fragrance (0.01% to 1.4%)
Lotion Sanitizer
Benzalkonium Chloride 0.13%
Water (60% to 95%)
Tetrasodium EDTA (0.001% to about 0.1%)
Cetrimonium Chloride (1% to 9%)
Behentrimonium Methosulfate (1% to 9%)
Glycerin (0.1% to 1.4%)
Dimethicone (0.5% to 4%)
Polysorbate 20 (0.1% to 4%)
Hydroxyethyl Ethylcellusose (0.1% to 2.4%)
12 cell building mineral salts (0.1% to 1.4%)
Allantoin (0.1% to 1.4%)
Aloe Vera Gel (0.1% to 1.4%)
Vitamin E Acetate (0.1% to 1.4%)
Benzathonium Chloride (0.1% to 1.9%)
Phenoxyehtanol (0.1% to 1.4%)
Caprylyl Glycol (0.1% to 1.4%)
Hyaluronic Acid (0.02% to 2.0%)
Fragrance (0.01% to 1.4%)
Gel Sanitizer
Benzalkonium Chloride 0.13%
Water (60% to 95%)
Tetrasodium EDTA (0.001% to about 0.1%)
Carbomer (0.01% to 1.4%)
Cetrimonium Chloride (1% to 9%)
Glycerin (0.1% to 1.4%)
Polysorbate 20 (0.1% to 1.4%)
12 cell building mineral salts (0.1% to 1.4%)
Allantoin (0.1% to 1.4%)
Aloe Vera Gel (0.1% to 1.4%)
Vitamin E Acetate (0.1% to 1.4%)
Benzathonium Chloride (0.1% to 1.9%)
Hyaluronic Acid (0.02% to 2.0%)
Fragrance (0.01% to 1.4%)

Figure 2:
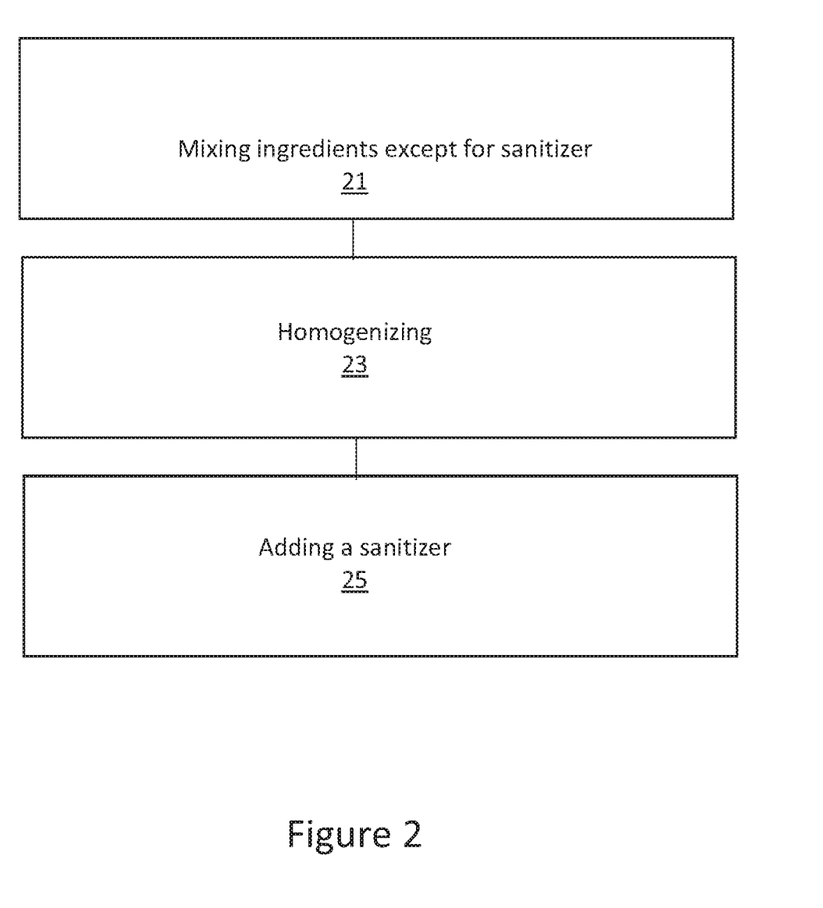
FIG. 2 is a flowchart of a method of manufacturing a hand sanitizer, according to one embodiment of the invention.

FIG. 2 shows flowchart showing a method of making a hand sanitizer composition, according to one embodiment of the invention. There is shown the steps of mixing ingredients except for sanitizer 21, homogenizing 23, and adding sanitizer 25.

The step of mixing may include mixing together in a vessel, using heat as needed:
 a. water as a solvent and carrier from about 60% to about 96% by weight sufficient to operate as a carrier and solvent for the composition;
 b. Tetrasodium EDTA from about 0.001% to about 0.1%, by weight;
 c. Benzathonium Chloride as a preservative from about 0.1% to about 1.0% by weight;
 d. a conditioner selected from the group of conditioners consisting of: Stearylkonium Chloride, Behentrimonium Chloride and Cetrimonium Chloride from an amount of about 0.1% to about 9% by weight;
 e. Glycerin from about 0.1% to about 1.4% by weight.
 f. a surfactant from about 0.02% to about 7.9% by weight;
 g. mineral salts from about 0.1% to about 1.4% by weight;
 h. a skin protectant from about 0.1% to about 1.4% by weight;
 i. an antioxidant vitamin from about 0.01% to about 1.4% by weight;

The step of homogenizing may include stirring, forcing the mixture at high pressure through small holes, using extruders, hammermills, colloid mills, ultrasonic homogenizers, and the like as appropriate for the ingredients.

The step of adding the sanitizer may include adding, sufficiently slowly while mixing to prevent undesired effects, a sanitizer selected from the group of sanitizers consisting of: Benzalkonium Chloride and Benzathonium Chloride from an amount of about 0.01% to about 0.13% by weight sufficient to sanitize hands during the use of the composition.

The term "sanitizer," as used herein, refers to an agent that reduces the number of bacterial contaminants to safe levels as judged by public health requirements. The recitation of numerical ranges by endpoints includes all numbers subsumed within that range (e.g., 1 to 5 includes 1, 1.5, 2, 2.75, 3, 3.80, 4, and 5).

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A hand sanitizing composition, comprising:
   a. water from about 75% to about 96% by weight sufficient to operate as a carrier and solvent for the composition;
   b. Tetrasodium EDTA from about 0.001% to about 01%, by weight;
   c. Benzethonium Chloride as a preservative from about 0.1% to about 1.0% by weight;
   d. a conditioner selected from the group consisting of: Stearylkonium Chloride, Behentrimonium Chloride and Cetrimonium Chloride from an amount of about 0.1% to about 9% by weight;
   e. a surfactant from about 0.02% to about 7.9% by weight;
   f. mineral salts from about 0.1% to about 1.4% by weight;
   g. a skin protectant from about 0.1% to about 1.4% by weight;
   h. an antioxidant vitamin from about 0.01% to about 1.4% by weight; and
   i. Benzalkonium Chloride from about 0.01% to about 0.13% by weight, sufficient to sanitize hands during the use of the composition.

2. The composition of claim 1, wherein the conditioner is Cetrimonium Chloride in an amount of between about 1% and about 9% by weight.

3. The composition of claim 1, wherein the surfactant is Polysorbate 20 in an amount of between about 0.1% to about 1.4% by weight.

4. The composition claim 1, wherein the mineral salts comprise Calcium Fluoride, Calcium Phosphate, Calcium Sulphate, iron Phosphate, Potassium Chloride, Potassium Phosphate, Potassium Sulphate, Magnesium Phosphate, Sodium Chloride, Sodium Phosphate, Sodium Sulphate, and Silicon Dioxide.

5. The composition of claim 1, wherein the mineral salts comprise at least one of Calcium Fluoride, Calcium Phosphate, Calcium Sulphate, Iron Phosphate, Potassium Chloride, Potassium Phosphate, Potassium Sulphate, Magnesium Phosphate, Sodium Chloride, Sodium Phosphate, Sodium Sulphate, and Silicon Dioxide.

6. The composition of claim 1, wherein the skin protectant is Allantoin.

7. The composition of claim 1, further comprising Aloe Vera gel from about 0.1% to about 1.4% by weight.

8. The composition of claim 1, wherein the antioxidant vitamin is Vitamin E Acetate.

9. The composition of claim 1, further comprising Hyaluronic Acid from about 0.02% to about 2.0% by weight.

10. The composition of claim 1, further comprising Cocamidopropyl Betaine from about 0.4% to about 3.0% by weight.

11. The composition of claim 1, further comprising Behentrimonium Methosulfate from about 1.0% to about 9.0% by weight.

12. The composition of claim 1, further comprising Dimethicone from about 0.5% to about 4.0% by weight.

13. The composition of claim 1, further comprising Hydroxyethyl Ethyl from about 0.1% to about 2.4% by weight.

14. The composition of claim 1, further comprising Phenoxyethanol from about 0.1% to about 1.4% by weight.

15. The composition of claim 1, further comprising Caprylyl Glycol from about 0.1% to about 1.4% by weight.

16. The composition of claim 1, further comprising Carbomer from about 0.01% to about 1.4% by weight.

17. An alcohol-free forming, lotion, or gel hand sanitizing composition, consisting essentially of:
   a. water from about 75% to about 96% by weight sufficient to operate as a carrier and solvent for the composition;
   b. Tetrasodium EDTA from about 0.001% to about 0.1%, by weight;
   c. Benzethonium Chloride as a preservative from about 0.1% to about 1.0% by weight;
   d. a conditioner selected from the group consisting of: Stearylkonium Chloride, Behentrimonium Chloride and Cetrimonium Chloride from an amount of about 0.0% to about 9% by weight;
   e. Glycerin from about 0.0% to about 1.4% by weight;
   f. a surfactant from about 0.02% to about 7.9% by weight;
   g. mineral salts from about 0.1% to about 1.4% by weight;
   h. a skin protectant from about 0.0% to about 1.4% by weight;
   i. an antioxidant vitamin from about 0.01% to about 1.4% by weight; and
   j. Benzalkonium Chloride from about 0.01% to about 0.13% by weight, sufficient to sanitize hands during the use of the composition.

18. A method of manufacturing a hand sanitizer composition, comprising the steps of:
   a. mixing together in a vessel, with applying heat as needed:
      i. water from about 75% to about 96% by weight sufficient to operate as a carrier and solvent for the composition;
      ii. Tetrasodium EDTA from about 0.001% to about 0.1%, by weight;
   b. mixing together in a vessel together with the already mixed water and Tetrasodium EDTA, with applying heat as needed:
      i. Benzethonium Chloride as a preservative from about 0.1% to about 1.0% by weight;
      ii. a conditioner selected from the group consisting of: Stearylkonium Chloride, Behentrimonium Chloride and Cetrimonium Chloride from an amount of about 0.1% to about 9% by weight;
      iii. Glycerin from about 0.1% to about 1.4% by weight;
      iv. a surfactant from about 0.02% to about 7.9% by weight;
      v. mineral salts from about 0.1% to about 1.4% by weight;
      vi. an antioxidant vitamin from about 0.01% to about 1.4% by weight;
   c. then homogenizing; and
   D. then adding a sanitizer selected from the group consisting of Benzalkonium Chloride and Benzathonium Chloride from an amount of about 0.01% to about 0.13% by weight sufficient to sanitize hands during the use of the composition.

* * * * *